US012788417B2

(12) United States Patent
Schuler et al.

(10) Patent No.: US 12,788,417 B2
(45) Date of Patent: Nov. 10, 2026

(54) METHOD AND APPARATUS FOR INSERTING A BONE PLATE

(71) Applicant: GLOBUS MEDICAL, INC., Audubon, PA (US)

(72) Inventors: Olivia Schuler, Levittown, PA (US); Gabrielle Zingalis, Philadelphia, PA (US); Evan Langdale, Philadelphia, PA (US); Peter Evans, Lafayette Hill, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 19/052,736

(22) Filed: Feb. 13, 2025

(65) Prior Publication Data

US 2025/0176978 A1 Jun. 5, 2025

Related U.S. Application Data

(63) Continuation of application No. 18/490,948, filed on Oct. 20, 2023, now Pat. No. 12,245,776, which is a continuation of application No. 17/486,154, filed on Sep. 27, 2021, now Pat. No. 11,826,060, which is a continuation of application No. 16/668,824, filed on Oct. 30, 2019, now Pat. No. 11,129,627.

(51) Int. Cl.

| | |
|---|---|
| ***A61B 17/80*** | (2006.01) |
| ***A61B 17/16*** | (2006.01) |
| ***A61B 17/17*** | (2006.01) |
| ***A61B 17/84*** | (2006.01) |

(52) U.S. Cl.

CPC .......... *A61B 17/17* (2013.01); *A61B 17/1637* (2013.01); *A61B 17/8061* (2013.01); *A61B 17/808* (2013.01); *A61B 17/84* (2013.01)

(58) Field of Classification Search

CPC ... A61B 17/7059; A61B 17/808; A61B 17/88; A61B 17/8872; A61B 2017/90

See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |

(Continued)

FOREIGN PATENT DOCUMENTS

| | | | |
|---|---|---|---|
| CN | 201987653 | U | 9/2011 |
| CN | 202313691 | U | 7/2012 |

(Continued)

*Primary Examiner* — Matthew J Lawson

(57) ABSTRACT

Devices, systems, and methods for locking a drill guide into a polyaxial hole while maintaining the form and function of the polyaxial hole are provided herein. In some embodiments, the drill guide includes a hollow outer body extending from a proximal end to a distal end and having a slot disposed proximate the proximate end, wherein the distal end is configured as a reverse collet having a plurality of prongs; an inner body having a central channel extending therethrough; and a lever coupled to the inner body through the slot, wherein the slot is shaped such that rotation of the lever results in motion along a central axis of the drill guide, and wherein a distal end of the inner body is configured to prevent radially inward deflection of the plurality of prongs when the inner body is in a lowermost position.

10 Claims, 12 Drawing Sheets

(56) References Cited

U.S. PATENT DOCUMENTS

| | | | |
|---|---|---|---|
| 3,463,148 | A | 8/1969 | Treace |
| 3,695,259 | A | 10/1972 | Yost |
| 3,716,050 | A | 2/1973 | Johnston |
| 4,187,840 | A | 2/1980 | Watanabe |
| 4,219,015 | A | 8/1980 | Steinemann |
| 4,493,317 | A | 1/1985 | Klaue |
| 4,524,765 | A | 6/1985 | de Zbikowski |
| 4,651,724 | A | 3/1987 | Berentey et al. |
| 4,683,878 | A | 8/1987 | Carter |
| 4,781,183 | A | 11/1988 | Casey et al. |
| 4,867,144 | A | 9/1989 | Karas et al. |
| 4,923,471 | A | 5/1990 | Morgan |
| 4,966,599 | A | 10/1990 | Pollock |
| 5,002,544 | A | 3/1991 | Klaue et al. |
| 5,041,114 | A | 8/1991 | Chapman et al. |
| 5,151,103 | A | 9/1992 | Tepic et al. |
| 5,259,398 | A | 11/1993 | Vrespa |
| 5,364,399 | A | 11/1994 | Lowery et al. |
| 5,372,598 | A | 12/1994 | Luhr et al. |
| 5,423,826 | A | 6/1995 | Coates et al. |
| 5,468,242 | A | 11/1995 | Reisberg |
| D365,634 | S | 12/1995 | Morgan |
| 5,489,305 | A | 2/1996 | Morgan |
| 5,527,311 | A | 6/1996 | Procter et al. |
| 5,578,036 | A | 11/1996 | Stone et al. |
| 5,601,553 | A | 2/1997 | Trebing et al. |
| 5,676,667 | A | 10/1997 | Hausman |
| 5,690,631 | A | 11/1997 | Duncan et al. |
| 5,709,686 | A | 1/1998 | Talos et al. |
| 5,709,687 | A | 1/1998 | Pennig |
| 5,718,704 | A | 2/1998 | Medoff |
| 5,718,705 | A | 2/1998 | Sammarco |
| 5,746,742 | A | 5/1998 | Runciman et al. |
| 5,766,175 | A | 6/1998 | Martinotti |
| 5,766,176 | A | 6/1998 | Duncan |
| 5,779,706 | A | 7/1998 | Tschakaloff |
| 5,785,712 | A | 7/1998 | Runciman et al. |
| 5,797,914 | A | 8/1998 | Leibinger |
| 5,814,048 | A | 9/1998 | Morgan |
| 5,925,048 | A | 7/1999 | Ahmad et al. |
| 5,938,664 | A | 8/1999 | Winquist et al. |
| 5,961,519 | A | 10/1999 | Bruce et al. |
| 5,980,540 | A | 11/1999 | Bruce |
| 6,001,099 | A | 12/1999 | Huebner |
| 6,071,291 | A | 6/2000 | Forst et al. |
| 6,093,201 | A | 7/2000 | Cooper et al. |
| 6,096,040 | A | 8/2000 | Esser |
| 6,107,718 | A | 8/2000 | Schustek et al. |
| 6,152,927 | A | 11/2000 | Farris et al. |
| 6,206,881 | B1 | 3/2001 | Frigg et al. |
| 6,283,969 | B1 | 9/2001 | Grusin et al. |
| 6,309,393 | B1 | 10/2001 | Tepic et al. |
| 6,322,562 | B1 | 11/2001 | Wolter |
| 6,364,882 | B1 | 4/2002 | Orbay |
| D458,683 | S | 6/2002 | Bryant et al. |
| D458,684 | S | 6/2002 | Bryant et al. |
| 6,533,786 | B1 | 3/2003 | Needham et al. |
| D479,331 | S | 9/2003 | Pike et al. |
| 6,623,486 | B1 | 9/2003 | Weaver et al. |
| 6,669,700 | B1 | 12/2003 | Farris et al. |
| 6,669,701 | B2 | 12/2003 | Steiner et al. |
| 6,712,820 | B2 | 3/2004 | Orbay |
| 6,719,759 | B2 | 4/2004 | Wagner et al. |
| 6,730,091 | B1 | 5/2004 | Pfefferle et al. |
| 6,866,665 | B2 | 3/2005 | Orbay |
| 6,955,677 | B2 | 10/2005 | Dahners |
| 6,974,461 | B1 | 12/2005 | Wolter |
| 7,001,387 | B2 | 2/2006 | Farris et al. |
| 7,063,701 | B2 | 6/2006 | Michelson |
| 7,090,676 | B2 | 8/2006 | Huebner et al. |
| 7,128,744 | B2 | 10/2006 | Weaver et al. |
| 7,137,987 | B2 | 11/2006 | Patterson et al. |
| 7,153,309 | B2 | 12/2006 | Huebner et al. |
| 7,179,260 | B2 | 2/2007 | Gerlach et al. |
| 7,250,053 | B2 | 7/2007 | Orbay |
| 7,294,130 | B2 | 11/2007 | Orbay |
| 7,322,983 | B2 | 1/2008 | Harris |
| 7,341,589 | B2 | 3/2008 | Weaver et al. |
| 7,344,538 | B2 | 3/2008 | Myerson et al. |
| 7,354,441 | B2 | 4/2008 | Frigg |
| 7,604,657 | B2 | 10/2009 | Orbay et al. |
| 7,632,277 | B2 | 12/2009 | Woll et al. |
| 7,635,381 | B2 | 12/2009 | Orbay |
| 7,637,928 | B2 | 12/2009 | Fernandez |
| 7,655,029 | B2 | 2/2010 | Niedernberger et al. |
| 7,655,047 | B2 | 2/2010 | Swords |
| 7,695,472 | B2 | 4/2010 | Young |
| 7,717,946 | B2 | 5/2010 | Oepen et al. |
| 7,722,653 | B2 | 5/2010 | Young et al. |
| 7,740,648 | B2 | 6/2010 | Young et al. |
| D622,853 | S | 8/2010 | Raven, III |
| 7,771,457 | B2 | 8/2010 | Kay et al. |
| 7,776,076 | B2 | 8/2010 | Grady, Jr. et al. |
| 7,857,838 | B2 | 12/2010 | Orbay |
| 7,867,260 | B2 | 1/2011 | Meyer et al. |
| 7,867,261 | B2 | 1/2011 | Sixto, Jr. et al. |
| 7,875,062 | B2 | 1/2011 | Lindemann et al. |
| 7,905,910 | B2 | 3/2011 | Gerlach et al. |
| 7,909,858 | B2 | 3/2011 | Gerlach et al. |
| 7,951,178 | B2 | 5/2011 | Jensen |
| 7,951,179 | B2 | 5/2011 | Matityahu |
| 7,976,570 | B2 | 7/2011 | Wagner et al. |
| D643,121 | S | 8/2011 | Millford et al. |
| D646,785 | S | 10/2011 | Milford |
| 8,043,297 | B2 | 10/2011 | Grady, Jr. et al. |
| 8,057,520 | B2 | 11/2011 | Ducharme et al. |
| 8,062,296 | B2 | 11/2011 | Orbay et al. |
| 8,100,953 | B2 | 1/2012 | White et al. |
| 8,105,367 | B2 | 1/2012 | Austin et al. |
| 8,114,081 | B2 | 2/2012 | Kohut et al. |
| 8,118,846 | B2 | 2/2012 | Leither et al. |
| 8,118,848 | B2 | 2/2012 | Ducharme et al. |
| 8,162,950 | B2 | 4/2012 | Digeser et al. |
| 8,167,918 | B2 | 5/2012 | Strnad et al. |
| 8,177,820 | B2 | 5/2012 | Anapliotis et al. |
| 8,231,627 | B2 | 7/2012 | Huebner et al. |
| 8,246,661 | B2 | 8/2012 | Beutter et al. |
| 8,252,032 | B2 | 8/2012 | White et al. |
| 8,257,403 | B2 | 9/2012 | Den Hartog et al. |
| 8,257,405 | B2 | 9/2012 | Haidukewych et al. |
| 8,257,406 | B2 | 9/2012 | Kay et al. |
| 8,262,707 | B2 | 9/2012 | Huebner et al. |
| 8,267,972 | B1 | 9/2012 | Gehlert |
| 8,317,842 | B2 | 11/2012 | Graham et al. |
| 8,323,321 | B2 | 12/2012 | Gradl |
| 8,337,535 | B2 | 12/2012 | White et al. |
| 8,343,155 | B2 | 1/2013 | Fisher et al. |
| 8,382,807 | B2 | 2/2013 | Austin et al. |
| 8,394,098 | B2 | 3/2013 | Orbay et al. |
| 8,394,130 | B2 | 3/2013 | Orbay et al. |
| 8,398,685 | B2 | 3/2013 | McGarity et al. |
| 8,403,966 | B2 | 3/2013 | Ralph et al. |
| 8,419,775 | B2 | 4/2013 | Orbay et al. |
| 8,435,272 | B2 | 5/2013 | Dougherty et al. |
| 8,439,918 | B2 | 5/2013 | Gelfand |
| 8,444,679 | B2 | 5/2013 | Ralph et al. |
| 8,491,593 | B2 | 7/2013 | Prien et al. |
| 8,506,608 | B2 | 8/2013 | Cerynik et al. |
| 8,512,384 | B2 | 8/2013 | Beutter et al. |
| 8,512,385 | B2 | 8/2013 | White et al. |
| 8,518,090 | B2 | 8/2013 | Huebner et al. |
| 8,523,862 | B2 | 9/2013 | Murashko, Jr. |
| 8,523,919 | B2 | 9/2013 | Huebner et al. |
| 8,523,921 | B2 | 9/2013 | Horan et al. |
| 8,540,755 | B2 | 9/2013 | Whitmore |
| 8,551,095 | B2 | 10/2013 | Fritzinger et al. |
| 8,551,143 | B2 | 10/2013 | Norris et al. |
| 8,568,462 | B2 | 10/2013 | Sixto, Jr. et al. |
| 8,574,268 | B2 | 11/2013 | Chan et al. |
| 8,597,334 | B2 | 12/2013 | Mocanu |
| 8,603,147 | B2 | 12/2013 | Sixto, Jr. et al. |
| 8,617,224 | B2 | 12/2013 | Kozak et al. |
| 8,632,574 | B2 | 1/2014 | Kortenbach et al. |
| 8,641,741 | B2 | 2/2014 | Murashko, Jr. |

(56) References Cited

U.S. PATENT DOCUMENTS

| | | | |
|---|---|---|---|
| 8,641,744 | B2 | 2/2014 | Weaver et al. |
| 8,663,224 | B2 | 3/2014 | Overes et al. |
| 8,728,082 | B2 | 5/2014 | Fritzinger et al. |
| 8,728,126 | B2 | 5/2014 | Steffen |
| 8,740,905 | B2 | 6/2014 | Price et al. |
| 8,747,442 | B2 | 6/2014 | Orbay et al. |
| 8,764,751 | B2 | 7/2014 | Orbay et al. |
| 8,764,808 | B2 | 7/2014 | Gonzalez-Hernandez |
| 8,777,998 | B2 | 7/2014 | Daniels et al. |
| 8,790,376 | B2 | 7/2014 | Fritzinger et al. |
| 8,790,377 | B2 | 7/2014 | Ralph et al. |
| 8,808,333 | B2 | 8/2014 | Kuster et al. |
| 8,808,334 | B2 | 8/2014 | Strnad et al. |
| 8,834,532 | B2 | 9/2014 | Velikov et al. |
| 8,834,537 | B2 | 9/2014 | Castanada et al. |
| 8,852,246 | B2 | 10/2014 | Hansson |
| 8,852,249 | B2 | 10/2014 | Ahrens et al. |
| 8,864,802 | B2 | 10/2014 | Schwager et al. |
| 8,870,931 | B2 | 10/2014 | Dahners et al. |
| 8,888,825 | B2 | 11/2014 | Batsch et al. |
| 8,906,076 | B2 | 12/2014 | Mocanu et al. |
| 8,911,482 | B2 | 12/2014 | Lee et al. |
| 8,926,675 | B2 | 1/2015 | Leung et al. |
| 8,940,026 | B2 | 1/2015 | Hilse et al. |
| 8,940,028 | B2 | 1/2015 | Austin et al. |
| 8,940,029 | B2 | 1/2015 | Leung et al. |
| 8,951,291 | B2 | 2/2015 | Impellizzeri |
| 8,968,368 | B2 | 3/2015 | Tepic |
| 9,011,457 | B2 | 4/2015 | Grady, Jr. et al. |
| 9,023,052 | B2 | 5/2015 | Lietz et al. |
| 9,050,151 | B2 | 6/2015 | Schilter |
| 9,072,555 | B2 | 7/2015 | Michel |
| 9,072,557 | B2 | 7/2015 | Fierlbeck et al. |
| 9,107,678 | B2 | 8/2015 | Murner et al. |
| 9,107,711 | B2 | 8/2015 | Hainard |
| 9,107,713 | B2 | 8/2015 | Horan et al. |
| 9,107,718 | B2 | 8/2015 | Isch |
| 9,113,970 | B2 | 8/2015 | Lewis et al. |
| 9,149,310 | B2 | 10/2015 | Fritzinger et al. |
| 9,161,791 | B2 | 10/2015 | Frigg |
| 9,161,795 | B2 | 10/2015 | Chasbrummel et al. |
| 9,168,075 | B2 | 10/2015 | Dell'Oca |
| 9,179,950 | B2 | 11/2015 | Zajac et al. |
| 9,179,956 | B2 | 11/2015 | Cerynik et al. |
| 9,180,020 | B2 | 11/2015 | Gause et al. |
| 9,211,151 | B2 | 12/2015 | Weaver et al. |
| 9,259,217 | B2 | 2/2016 | Fritzinger et al. |
| 9,259,255 | B2 | 2/2016 | Lewis et al. |
| 9,271,769 | B2 | 3/2016 | Batsch et al. |
| 9,283,010 | B2 | 3/2016 | Medoff et al. |
| 9,295,506 | B2 | 3/2016 | Raven, III et al. |
| 9,314,284 | B2 | 4/2016 | Chan et al. |
| 9,320,554 | B2 | 4/2016 | Greenberg et al. |
| 9,322,562 | B2 | 4/2016 | Takayama et al. |
| 9,370,388 | B2 | 6/2016 | Globerman et al. |
| D765,851 | S | 9/2016 | Early et al. |
| 9,433,407 | B2 | 9/2016 | Fritzinger et al. |
| 9,433,452 | B2 | 9/2016 | Weiner et al. |
| 9,468,479 | B2 | 10/2016 | Marotta et al. |
| 9,480,512 | B2 | 11/2016 | Orbay |
| 9,486,262 | B2 | 11/2016 | Andermahr et al. |
| 9,492,213 | B2 | 11/2016 | Orbay |
| 9,510,878 | B2 | 12/2016 | Nanavati et al. |
| 9,510,880 | B2 | 12/2016 | Terrill et al. |
| 9,526,543 | B2 | 12/2016 | Castaneda et al. |
| 9,545,277 | B2 | 1/2017 | Wolf et al. |
| 9,549,819 | B1 | 1/2017 | Bravo et al. |
| 9,566,097 | B2 | 2/2017 | Fierlbeck et al. |
| 9,579,133 | B2 | 2/2017 | Guthlein |
| 9,622,799 | B2 | 4/2017 | Orbay et al. |
| 9,636,157 | B2 | 5/2017 | Medoff |
| 9,649,141 | B2 | 5/2017 | Raven, III et al. |
| 9,668,794 | B2 | 6/2017 | Kuster et al. |
| 9,801,670 | B2 | 10/2017 | Hashmi et al. |
| 9,814,504 | B2 | 11/2017 | Ducharme et al. |
| 10,159,514 | B2 | 12/2018 | Perrow et al. |
| 10,357,294 | B2 | 7/2019 | Medoff |
| 2002/0045901 | A1 | 4/2002 | Wagner et al. |
| 2002/0147450 | A1 | 10/2002 | Lehuec et al. |
| 2004/0097937 | A1 | 5/2004 | Pike et al. |
| 2005/0107796 | A1 | 5/2005 | Gerlach et al. |
| 2005/0131413 | A1 | 6/2005 | O'Driscoll et al. |
| 2005/0187551 | A1 | 8/2005 | Orbay et al. |
| 2006/0149265 | A1 | 7/2006 | James et al. |
| 2006/0241607 | A1 | 10/2006 | Myerson et al. |
| 2007/0173840 | A1 | 7/2007 | Huebner |
| 2007/0270849 | A1 | 11/2007 | Orbay et al. |
| 2007/0288022 | A1 | 12/2007 | Lutz |
| 2008/0021477 | A1 | 1/2008 | Strnad et al. |
| 2008/0234749 | A1 | 9/2008 | Forstein |
| 2008/0275510 | A1 | 11/2008 | Schonhardt et al. |
| 2009/0024172 | A1 | 1/2009 | Pizzicara |
| 2009/0024173 | A1 | 1/2009 | Reis, Jr. |
| 2009/0088768 | A1 | 4/2009 | Grant et al. |
| 2009/0118773 | A1 | 5/2009 | James et al. |
| 2009/0198285 | A1 | 8/2009 | Raven, III |
| 2009/0228010 | A1 | 9/2009 | Gonzalez-Hernandez et al. |
| 2009/0228047 | A1 | 9/2009 | Derouet et al. |
| 2009/0248084 | A1 | 10/2009 | Hintermann |
| 2009/0281543 | A1 | 11/2009 | Orbay et al. |
| 2009/0299369 | A1 | 12/2009 | Orbay et al. |
| 2009/0312760 | A1 | 12/2009 | Forstein et al. |
| 2010/0057086 | A1 | 3/2010 | Price et al. |
| 2010/0114097 | A1 | 5/2010 | Siravo et al. |
| 2010/0121326 | A1 | 5/2010 | Woll et al. |
| 2010/0274247 | A1 | 10/2010 | Grady, Jr. et al. |
| 2011/0106086 | A1 | 5/2011 | Laird |
| 2011/0218580 | A1 | 9/2011 | Schwager et al. |
| 2012/0010667 | A1 | 1/2012 | Eglseder |
| 2012/0059424 | A1 | 3/2012 | Epperly et al. |
| 2012/0203227 | A1 | 8/2012 | Martin |
| 2012/0232599 | A1 | 9/2012 | Schoenly et al. |
| 2012/0323284 | A1 | 12/2012 | Baker et al. |
| 2013/0018426 | A1 | 1/2013 | Tsai et al. |
| 2013/0046347 | A1 | 2/2013 | Cheng et al. |
| 2013/0060291 | A1 | 3/2013 | Petersheim |
| 2013/0123841 | A1 | 5/2013 | Lyon |
| 2013/0138156 | A1 | 5/2013 | Derouet |
| 2013/0150902 | A1 | 6/2013 | Leite |
| 2013/0165981 | A1 | 6/2013 | Clasbrummet et al. |
| 2013/0211463 | A1 | 8/2013 | Mizuno et al. |
| 2013/0261674 | A1 | 10/2013 | Fritzinger |
| 2013/0289630 | A1 | 10/2013 | Fritzinger |
| 2014/0005728 | A1 | 1/2014 | Koay et al. |
| 2014/0018862 | A1 | 1/2014 | Koay et al. |
| 2014/0031879 | A1 | 1/2014 | Sixto, Jr. et al. |
| 2014/0066998 | A1 | 3/2014 | Martin |
| 2014/0094856 | A1 | 4/2014 | Sinha |
| 2014/0121710 | A1 | 5/2014 | Weaver et al. |
| 2014/0180345 | A1 | 6/2014 | Chan et al. |
| 2014/0277178 | A1 | 9/2014 | O'Kane et al. |
| 2014/0277181 | A1 | 9/2014 | Garlock |
| 2014/0316473 | A1 | 10/2014 | Pfeffer et al. |
| 2014/0330320 | A1 | 11/2014 | Wolter |
| 2014/0378975 | A1 | 12/2014 | Castaneda et al. |
| 2015/0051650 | A1 | 2/2015 | Verstreken et al. |
| 2015/0051651 | A1 | 2/2015 | Terrill et al. |
| 2015/0073486 | A1 | 3/2015 | Marotta et al. |
| 2015/0080975 | A1 | 3/2015 | Pleil |
| 2015/0105829 | A1 | 4/2015 | Laird |
| 2015/0112355 | A1 | 4/2015 | Dahners et al. |
| 2015/0134011 | A1 | 5/2015 | Medoff |
| 2015/0142065 | A1 | 5/2015 | Schonhardt et al. |
| 2015/0190185 | A1 | 7/2015 | Koay et al. |
| 2015/0209091 | A1 | 7/2015 | Sixto, Jr. et al. |
| 2015/0216571 | A1 | 8/2015 | Impellizzeri |
| 2015/0223852 | A1 | 8/2015 | Lietz et al. |
| 2015/0272638 | A1 | 10/2015 | Langford |
| 2015/0282851 | A1 | 10/2015 | Michel |
| 2015/0313653 | A1 | 11/2015 | Ponce et al. |
| 2015/0313654 | A1 | 11/2015 | Horan et al. |
| 2015/0327898 | A1 | 11/2015 | Martin |
| 2015/0351816 | A1 | 12/2015 | Lewis et al. |
| 2015/0374421 | A1 | 12/2015 | Rocci et al. |

(56) References Cited

U.S. PATENT DOCUMENTS

| | | | |
|---|---|---|---|
| 2016/0022336 A1 | 1/2016 | Bateman | |
| 2016/0030035 A1 | 2/2016 | Zajac et al. | |
| 2016/0045237 A1 | 2/2016 | Cerynik et al. | |
| 2016/0045238 A1 | 2/2016 | Bohay et al. | |
| 2016/0074081 A1 | 3/2016 | Weaver et al. | |
| 2016/0166297 A1 | 6/2016 | Mighell et al. | |
| 2016/0166298 A1 | 6/2016 | Mighell et al. | |
| 2016/0183990 A1 | 6/2016 | Koizumi et al. | |
| 2016/0262814 A1 | 9/2016 | Wainscott | |
| 2016/0278828 A1 | 9/2016 | Ragghianti | |
| 2016/0310183 A1 | 10/2016 | Shah et al. | |
| 2016/0310185 A1 | 10/2016 | Sixto et al. | |
| 2016/0324552 A1 | 11/2016 | Baker et al. | |
| 2016/0354122 A1 | 12/2016 | Montello et al. | |
| 2017/0000534 A1* | 1/2017 | Medoff ................ | A61B 17/808 |
| 2017/0035478 A1 | 2/2017 | Andermahr et al. | |
| 2017/0042592 A1 | 2/2017 | Kim | |
| 2017/0042596 A9 | 2/2017 | Mighell et al. | |
| 2017/0049493 A1 | 2/2017 | Gauneau et al. | |
| 2017/0065312 A1 | 3/2017 | Lauf et al. | |
| 2017/0105775 A1 | 4/2017 | Ricker et al. | |
| 2017/0151064 A1 | 6/2017 | Armstrong et al. | |
| 2017/0215931 A1 | 8/2017 | Cremer et al. | |
| 2019/0046251 A1 | 2/2019 | Detweiler et al. | |
| 2019/0110821 A1 | 4/2019 | Perrow et al. | |
| 2019/0314042 A1* | 10/2019 | Laird, Jr. ............. | A61B 17/808 |

FOREIGN PATENT DOCUMENTS

| | | | |
|---|---|---|---|
| CN | 202821574 | U | 3/2013 |
| CN | 202821575 | U | 3/2013 |
| CN | 203506858 | U | 4/2014 |
| CN | 203815563 | U | 9/2014 |
| CN | 105982727 | A | 10/2016 |
| EP | 1661525 | A2 | 5/2006 |
| EP | 3552562 | A1 | 10/2019 |
| FR | 2846870 | A1 | 5/2004 |
| FR | 2928259 | A1 | 9/2009 |
| JP | 2003210478 | A | 7/2003 |
| JP | 2005511116 | A | 4/2005 |
| JP | 2006150055 | A | 6/2006 |
| JP | 2008212461 | A | 9/2008 |
| JP | 2009022734 | A | 2/2009 |
| JP | 2019181207 | A | 10/2019 |
| TW | 201316942 | A | 5/2013 |
| WO | 2016079504 | A1 | 5/2016 |

* cited by examiner

METHOD AND APPARATUS FOR INSERTING A BONE PLATE

REFERENCE TO RELATED APPLICATIONS

The present application is a continuation of U.S. patent application Ser. No. 18/490,948, filed on Oct. 20, 2023 and published as U.S. 2024-0138855, which is a continuation of U.S. patent application Ser. No. 17/486,154, filed on Sep. 27, 2021 and now U.S. Pat. No. 11,826,060, which is a continuation of U.S. patent application Ser. No. 16/668,824 filed on Oct. 30, 2019 and now U.S. Pat. No. 11,129,627, all of which are incorporated herein by reference in their entirety.

FIELD

The present disclosure relates to surgical devices, and more particularly, stabilization systems, for example, for trauma applications.

BACKGROUND

Bone fractures are often repaired by internal fixation of the bone, such as diaphyseal bone, using one or more plates. The plate is held against the fractured bone with screws, for example, which engage the bone and heads, which provide a compressive force against the plate. The plate and bone are thus forced against each other in a manner that transfers load primarily between a bone-contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. Of course, the designs of the plates may vary based on the location and type of fracture.

Without a handle attachment or similar apparatus, it can be difficult to maintain a firm grip on a plate during insertion of the plate through an incision, accurately place the plate, or apply any force(s) required for manipulation of the plate in different areas of the patient's body.

SUMMARY

To meet this and other needs, devices, systems, and methods for inserting a plate are provided herein. In some embodiments, an apparatus for inserting a bone plate to a target site, the apparatus includes a body extending from an upper end to a lower end; a plate receiving portion configured to receive the bone plate; and a plate engaging mechanism configured to couple the bone plate to the body, wherein the body includes a gripping surface configured to be gripped by a user's hand.

BRIEF DESCRIPTION OF THE DRAWING

A more complete understanding of the present invention, and the attendant advantages and features thereof, will be more readily understood by reference to the following detailed description when considered in conjunction with the accompanying drawings wherein.

DETAILED DESCRIPTION

Figure 1A:
FIG. 1A depicts a trauma plate suitable for use with a plate inserter in accordance with embodiments of the present disclosure.

Embodiments of the disclosure are generally directed to devices, systems, and methods for inserting a plate through an incision and to a target area within a patient. Specifically, embodiments are directed to a plate inserter configured to advantageously allow for the plate to be coupled to the inserter on a back table or intra-operatively to an end of a plate opposite an end already fixed to bone. The inventive inserter also advantageously provides a low profile on the lowermost surface of the inserter (i.e., the portion that couples to the plate) to avoid soft tissue irritation, case of operation with one hand, and a comfortable grip that fits the contours of a user's hand.

Although the following description and the figures show a specific plate, it should be noted that the inventive plate inserter may be used with any type of plate. Exemplary plates may include plates adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plate may be curved, contoured, straight, or flat. The plate may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Figure 1B:
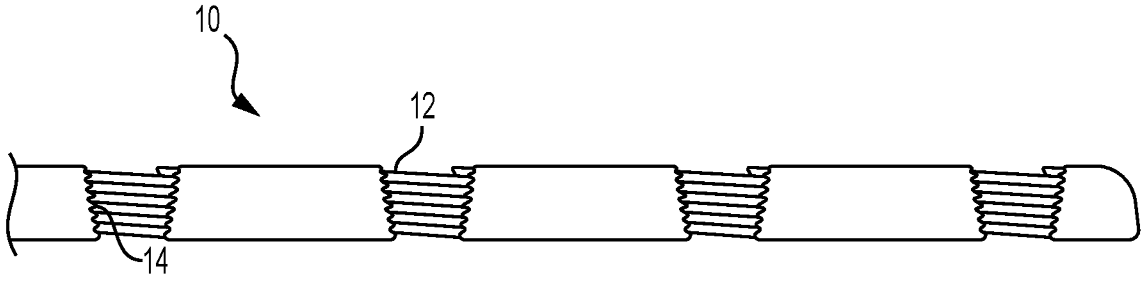
FIG. 1B is a cross-sectional view of the plate of FIG. 1A taken along line B-B'.

Referring now to the drawings, FIGS. 1A and 1B depict an elevated side view and a cross-sectional view, respectively, of a plate 10 including at least one opening such as, for example, a hole 12 (eight holes shown in FIG. 1A). The hole 12 extends through the plate 10 and is configured to accept a fastener (not shown) that is able to dynamically compress the bone and/or affix the plate 10 to the bone. As shown more clearly in FIG. 1B, the hole 12 may include threads 14 configured to correspond to threads of a fastener (not shown).

Figure 2:
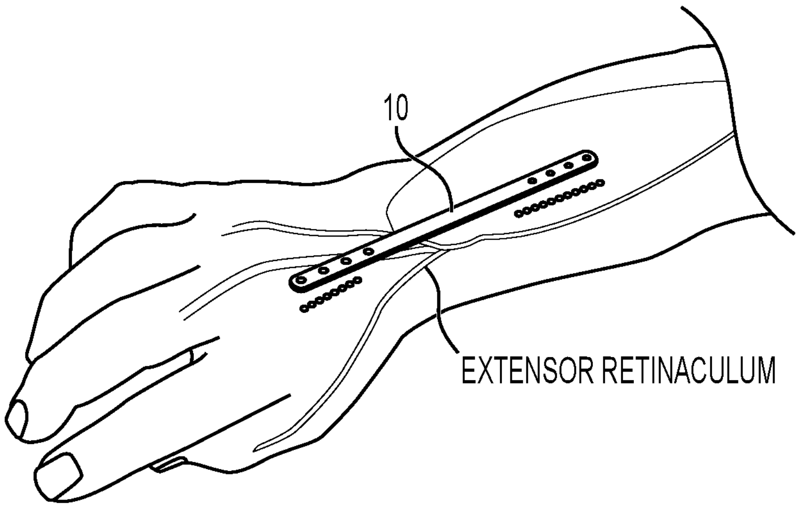
FIG. 2 depicts the trauma plate of FIGS. 1A and 1B implanted in a patient.
Figure 3:
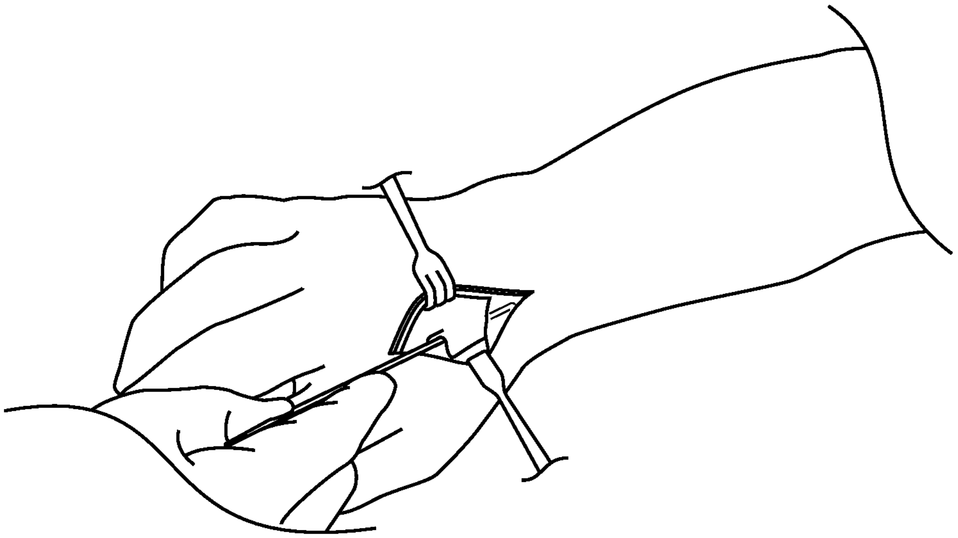
FIG. 3 depicts the retraction of patient anatomy to implant the trauma plate of FIGS. 1A and 1B.

FIG. 2 illustrate the plate 10 implanted along the dorsal side of a patient's hand. FIG. 3 depicts the retraction necessary to access the dorsal side of the patient's hand to implant the plate 10. The opening that permits access to the target site is extremely small. As such, it has been difficult to place and manipulate such a plate during the implantation process.

FIGS. 4A-4D depict a plate inserter 400 in accordance with embodiments of the present disclosure. In some embodiments, the plate insert 400 includes a body 402 extending from an upper end 404 to a lower end 406. The lower end 406 includes an opening 407 configured to receive a portion of the plate 10 to be held by the plate inserter 400. The body 402 further includes a gripping portion 408 configured to easily be gripped by a user's hand. A plate locking mechanism 410 is disposed within the body 402. In some embodiments, the plate locking mechanism 410 includes an actuator 412, which extends through the upper end 404. The actuator 412 includes a rotatable lever 414 coupled to an actuator body 416. The actuator body 416 includes a protruding element 418 that extends radially outward from the actuator body 416 into a groove 420 formed on an interior wall 422 of the body 402. The groove 420 is sloped such that when a user turns the lever 414 (and thus the actuator body 416) in a first direction (indicated by arrow A in FIG. 4B), movement of the protruding element 418 along the groove 420 forces the actuator body 416 to move downwards. Turning the lever 414 in a second direction (indicated by arrow B in FIG. 4C) opposite the first direction forces the actuator body 416 to move upwards.

Figure 4A:
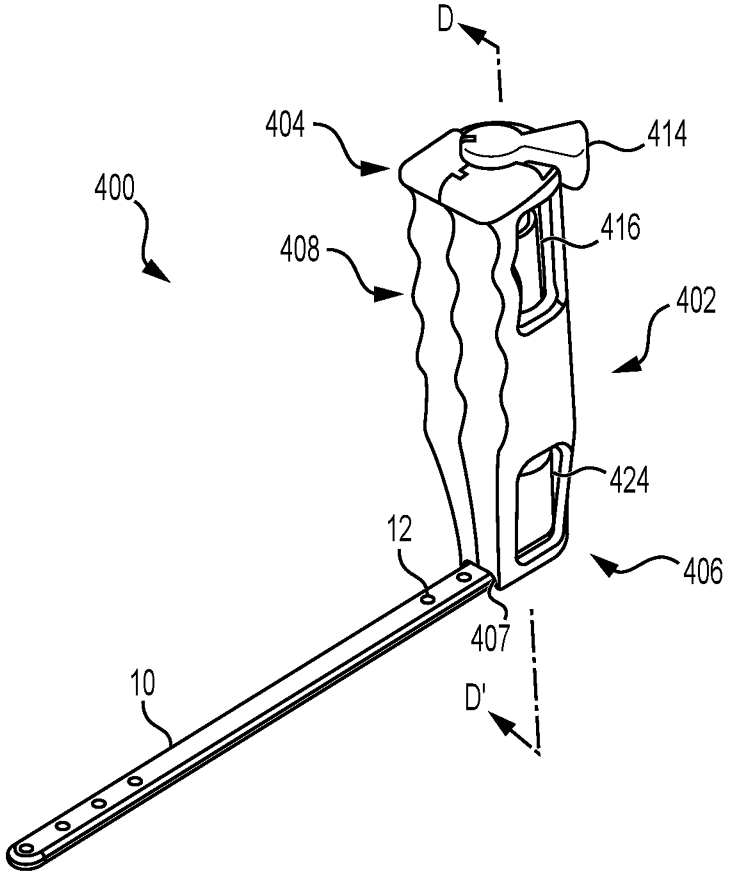
FIGS. 4A-4D depict an apparatus for inserting a plate in accordance with embodiments of the present disclosure.
Figure 4B:
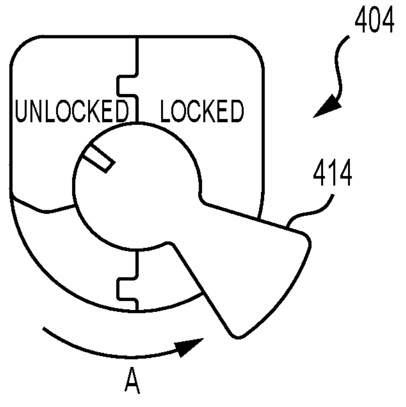
Figure 4C:
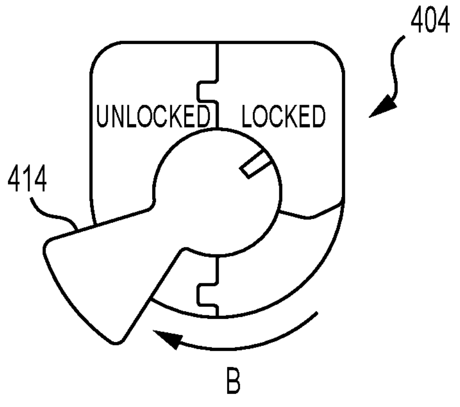
Figure 4D:
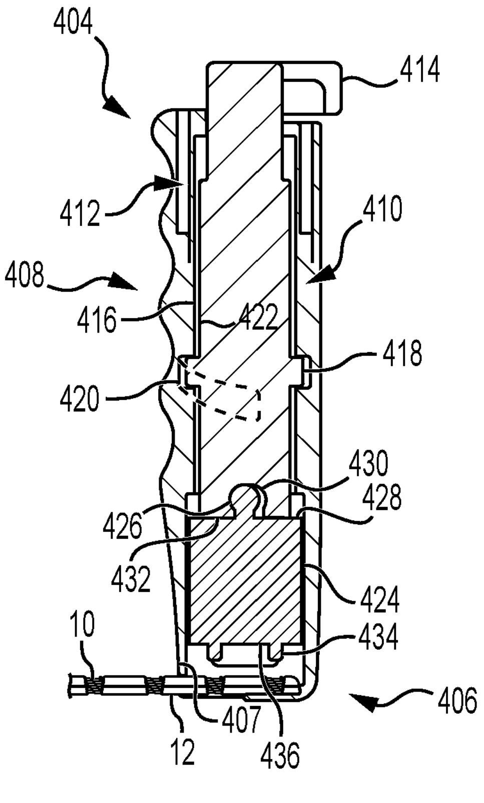

In some embodiments, the plate locking mechanism 410 further includes a plate engagement body 424 disposed beneath the actuator body 416. The plate engagement body 424 is coupled to the actuator body 416 in a way that allows the actuator body 416 to rotate relative to the plate engagement body. For example, as shown in FIG. 4D, the plate engagement body 424 may include a spherical protrusion 426 extending upwardly from an upper surface 428 of the plate engagement body 424 into a corresponding spherical recess 430 formed in a bottom surface 432 of the actuator body 416. Such a coupling enables the two bodies 416, 424 to be coupled, while allowing for the rotation of the actuator body 416 relative to the plate engagement body 424.

The plate engagement body 424 includes one or more engagement members 434 (two shown in FIG. 4D) extending downwardly from a bottom surface 436 of the plate engagement body 424. The engagement members 434 are configured to engage (i.e., be inserted into) the holes 12 of the plate 10. After the plate 10 is inserted into the opening 407, the holes 12 are disposed beneath the one or more engagement members 434. Rotation of the lever 414 in the first direction causes the actuator body 416 and the plate engagement body 424 downwards so that the one or more engagement members 434 are inserted into corresponding holes 12. The user may subsequently insert the plate 10 into patient and manipulate the plate as desired. When the user wishes to disengage the plate inserter 400 from the plate 10, the user rotates the lever 414 in the second direction so that the engagement members 434 retract upwards and out of engagement with the holes 12.

FIGS. 5A-5I depict a plate inserter 500 in accordance with embodiments of the present disclosure. In some embodiments, the plate inserter 500 includes a frame 502 and an actuator handle 504 rotatably coupled to the frame 502 via a pin connection 505. The frame 502 extends from an upper end 506 to a lower end 508. As shown more clearly in FIGS. 5A, 5C, and 5D, the lower end 508 includes a plate support base 510 having a groove 512 configured and dimensioned to receive the plate 10 therein. The actuator handle 504 also includes a gripping portion 509 configured to easily be gripped by a user's hand.

As shown more clearly in FIGS. 5C-5D and 5H-5I, the plate inserter 500 further includes an engagement body 514 disposed within the frame 502. A lower portion 516 of the actuator handle 504 extends into an opening 518 of the engagement body 514 to cause vertical movement of the engagement body 514, as will be described below. The engagement body 514 includes at least one engagement member 520 (two shown) extending downwardly from a bottom surface 522 of the engagement body 514. The engagement members 520 are configured to engage (i.e., be inserted into) the holes 12 of the plate 10. In use, the plate 10 is inserted into the groove 512 until it contacts a back wall 523 of the frame 502. Subsequently, the engagement members 520 are inserted into the holes 12 as described below.

In some embodiments, the plate inserter 500 includes a first torsion spring 524 mounted on a post 526 within the frame 502. A free end 528 of the torsion spring 524 is in contact with the actuator handle 504 to bias it towards the position shown in FIGS. 5H and 5I, in which the engagement members 520 do not engage the holes 12 of the plate 10. To move the engagement members 520 into the holes 12, thus fixing the plate 10 to the inserter 500, the user grips the gripping portion 509 and squeezes the actuator handle 504 in the direction indicated by arrow A (shown in FIGS. 5A and 5C). When this movement occurs, the actuator handle 504 rotates in a clockwise direction about the pin connection 505, thus moving the lower portion 516 away from a back wall 530 of the opening 518. The lower portion 516 includes a tip 532 that is shaped so that movement of the lower portion 516 away from the back wall 530 results in the tip 532 exerting a downward force on the engagement body 514, thus moving the engagement members 520 into the holes 10.

Figure 5A:
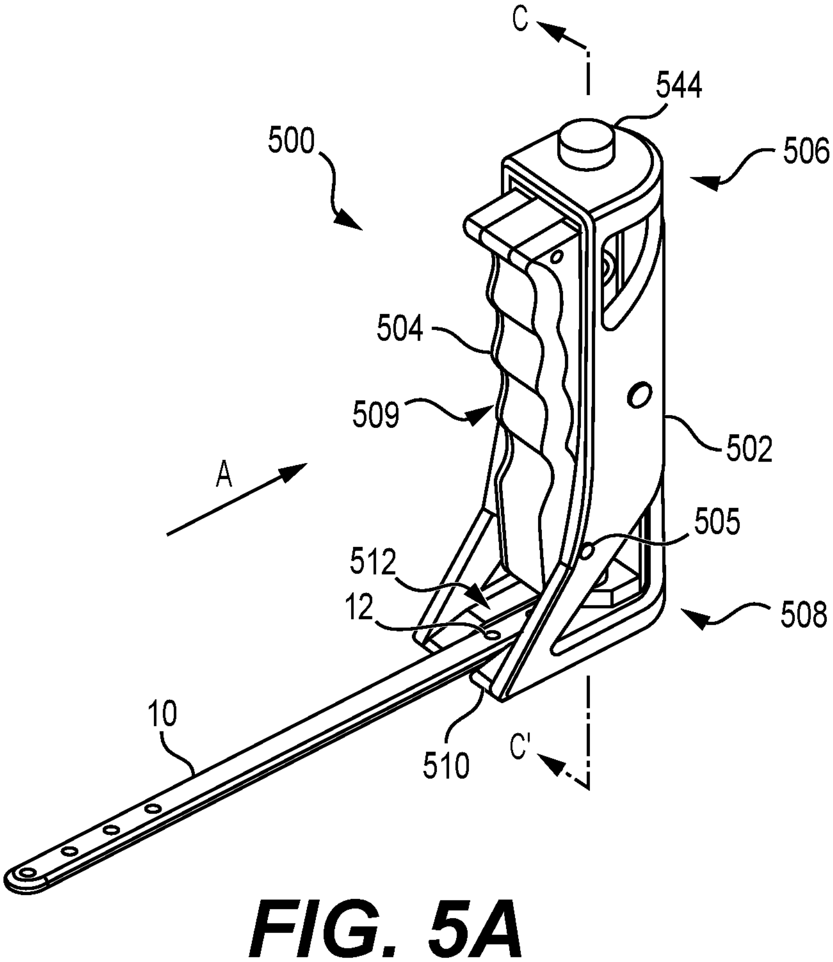
FIGS. 5A-5I depict an apparatus for inserting a plate in accordance with embodiments of the present disclosure.
Figure 5B:
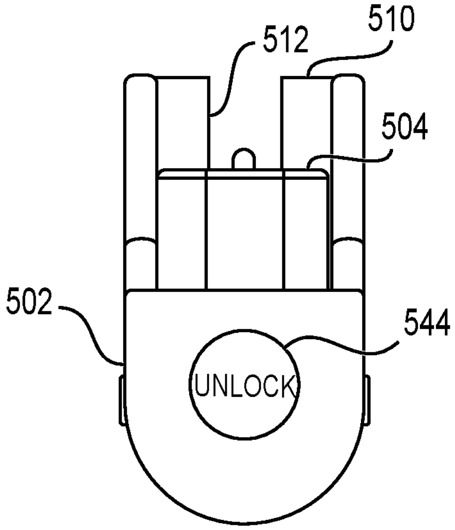
Figure 5D:
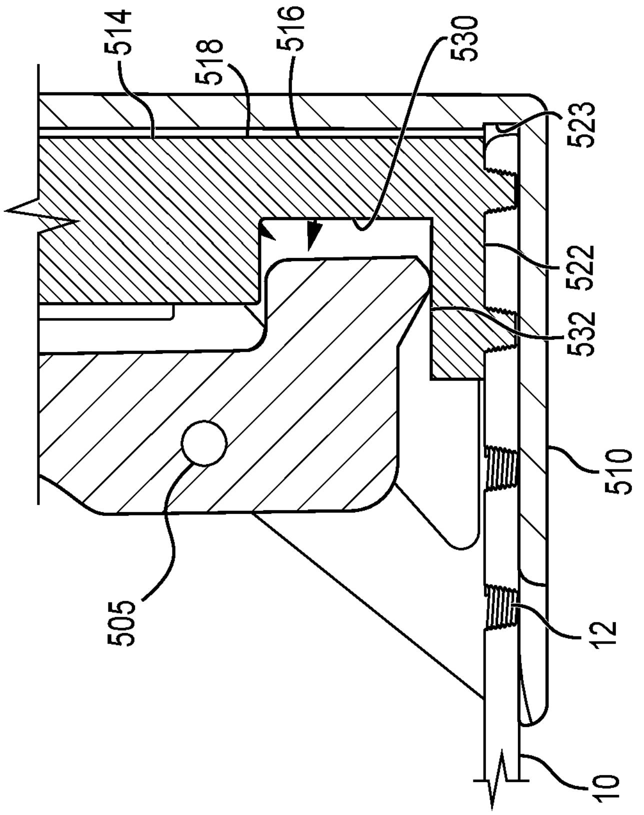
Figure 5C:
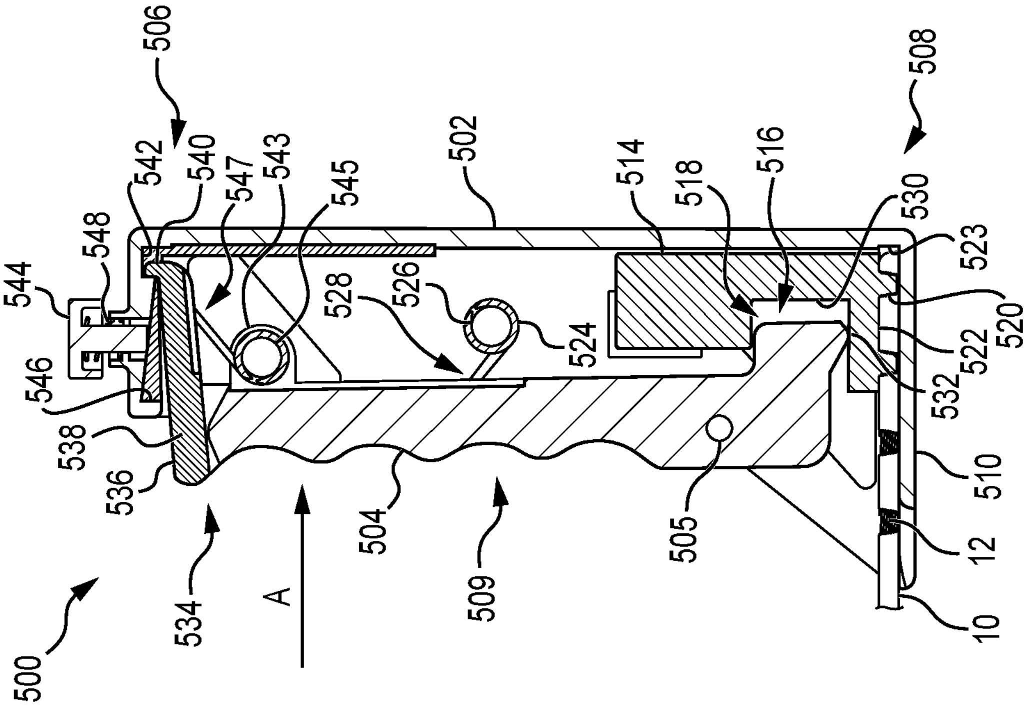
Figure 5F:
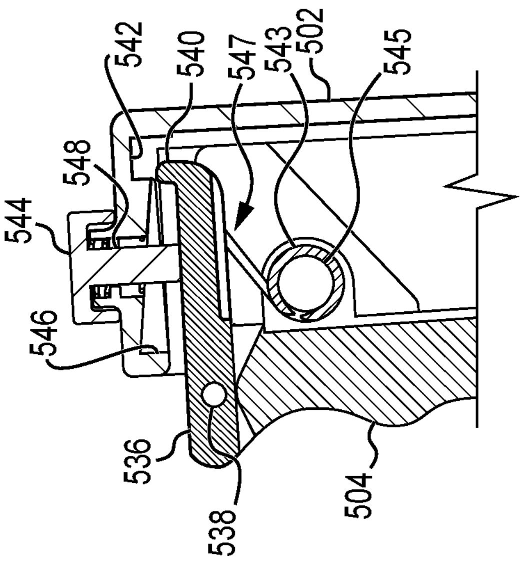
Figure 5E:
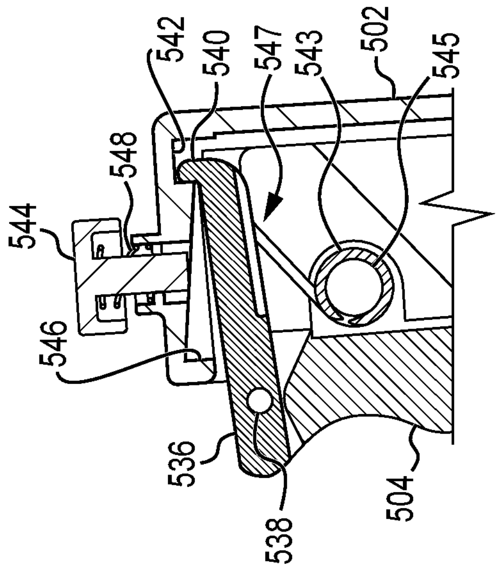
Figure 5G:
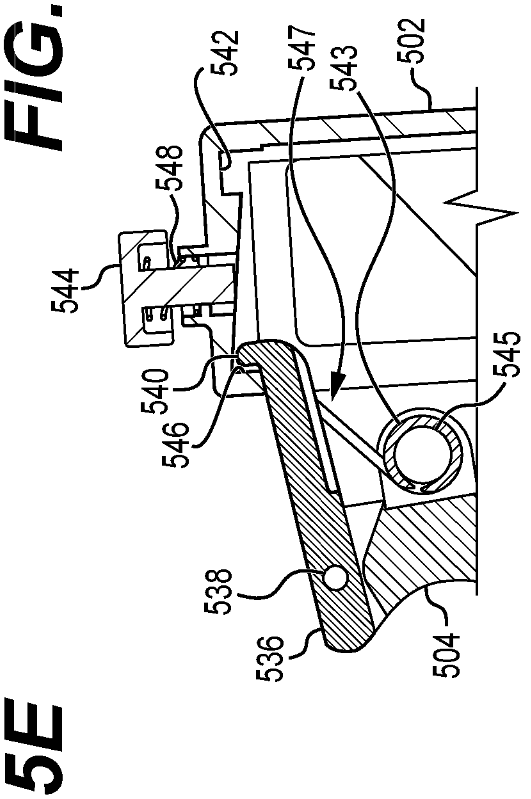
Figure 5I:
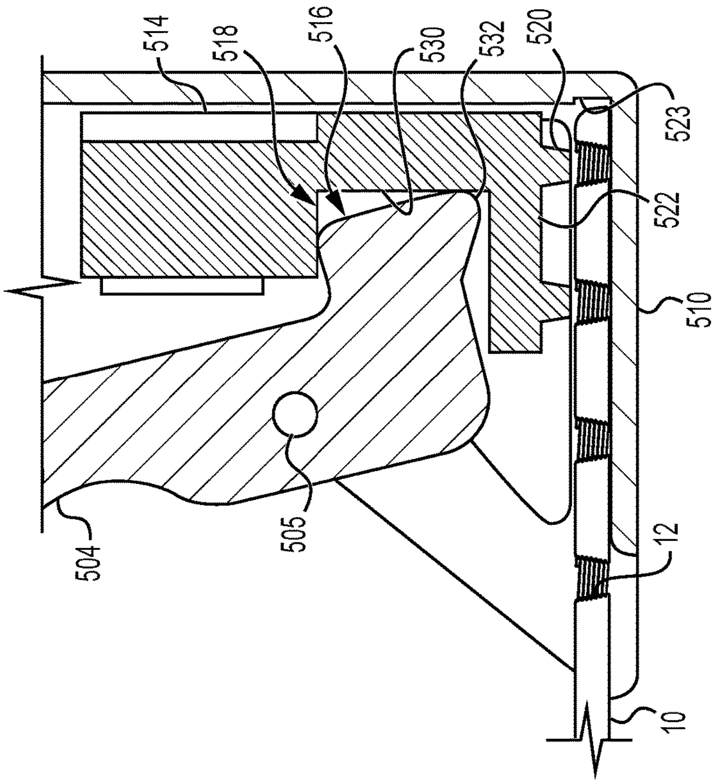
Figure 5H:
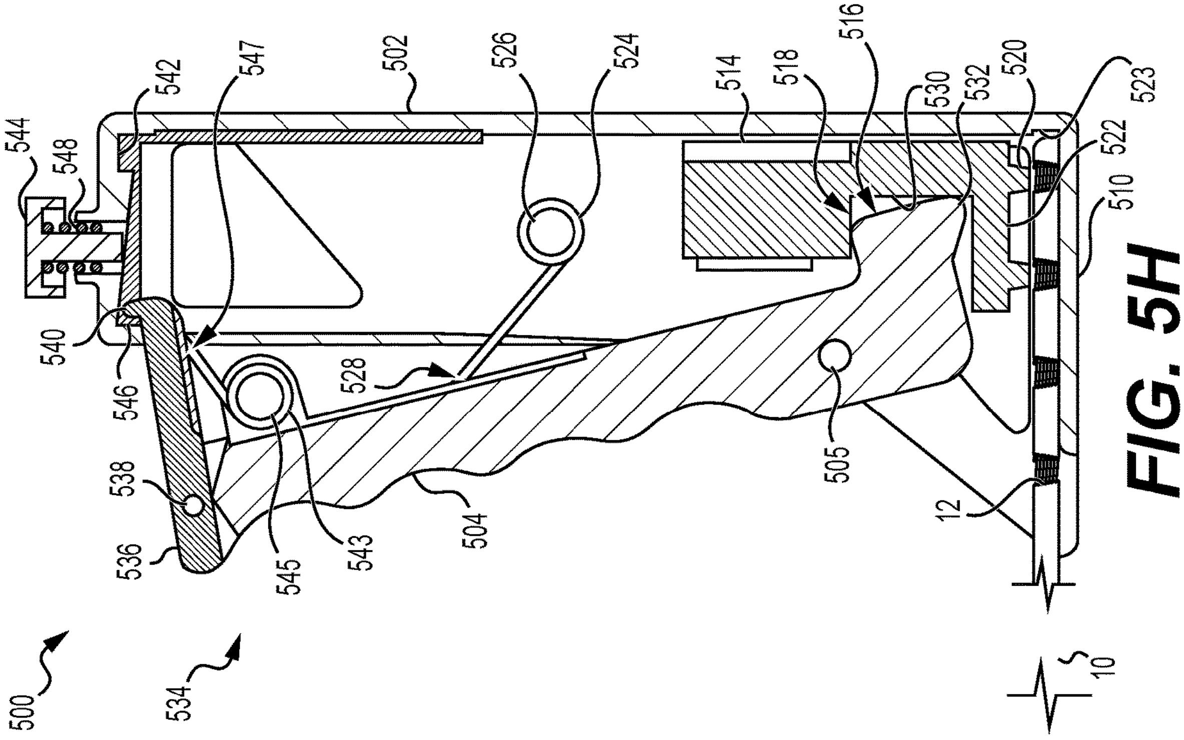

Referring to FIGS. 5E-5G, to retain the inserter 500 in the plate engagement position just described, an upper portion 534 of the actuator handle 504 includes a retention member 536 pivotally coupled to the upper portion 534 via a pin connection 538. The retention member 536 includes an upwardly extending lip 540 configured to be disposed in a corresponding retention recess 542 formed on the interior of the frame 502 when the inserter 500 is in the plate engagement position (shown in FIGS. 5C-5E). A second torsion spring 543 is coupled to the actuator handle 504 via a pin connection 545. A free end 547 of the torsion spring 543 contacts the retention member 536 and is configured to bias the retention member 536 upward. When the lip 540 of the retention member 542 is disposed within the retention recess 542 under the bias of the second torsion spring 536 (as shown in FIG. 5E), the inserter 500 is locked in the plate engagement position so that the plate 10 can be manipulated as desired.

To disengage the engagement members 520 from the holes 12, a button 544 disposed in the upper end 506 is pressed. Pressing the button 544 causes a lower portion of the button 544 to push down on the retention member 536 (as shown in FIG. 5F) to overcome the biasing force of the second torsion spring 543, thus moving the lip 540 out of the retention recess 542 (as shown in FIG. 5G). Under the biasing force of the first torsion spring 524, the actuator handle 504 returns to the disengaged position shown in FIG. 5H. In some embodiments, the frame 502 includes a lip 546 that retains the upwardly extending lip 540 when the actuator handle returns to the disengaged position (as shown in FIG. 5G). In some embodiments, a biasing element 548 (e.g., a helical spring) may be disposed between the button 544 and the frame 502 to bias the button 544 upwards such that the button 544 returns to its original position after it is pressed down to release the retention member 536.

Figure 6A:
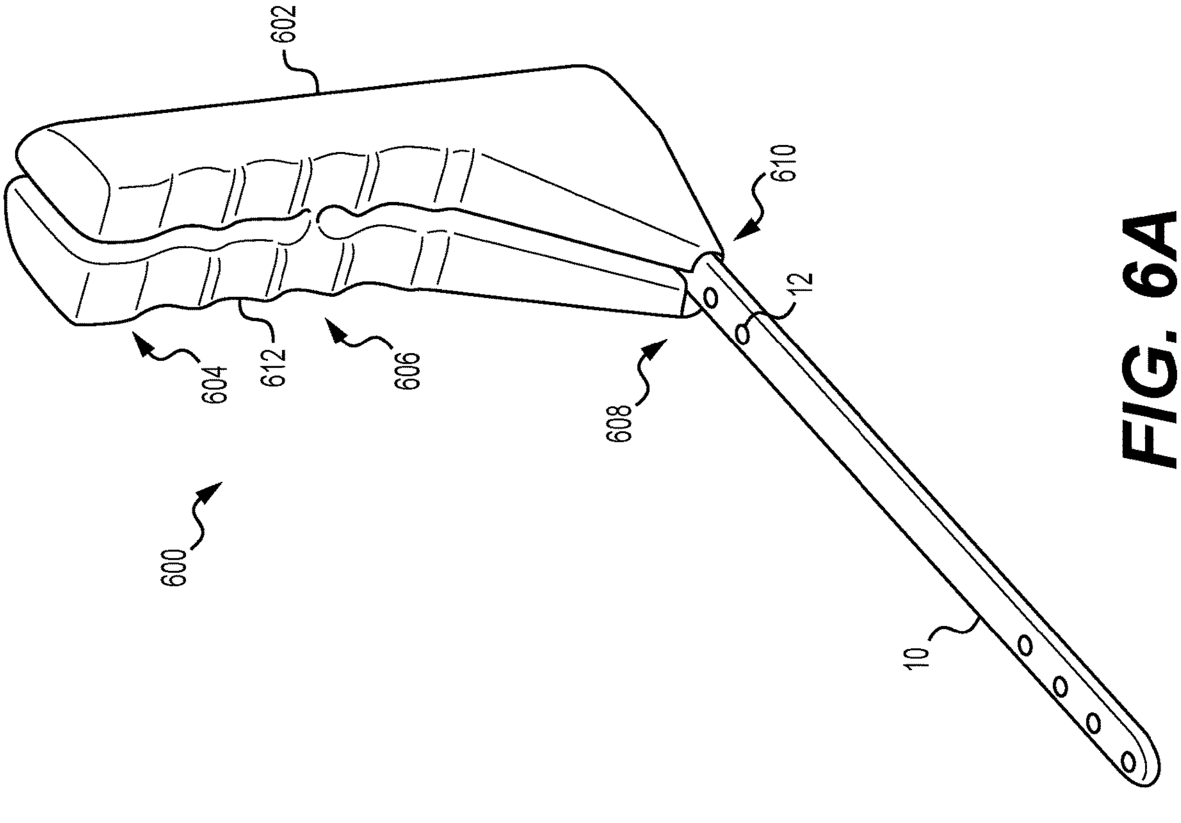
FIGS. 6A and 6B depict an apparatus for inserting a plate in accordance with embodiments of the present disclosure.
Figure 6B:
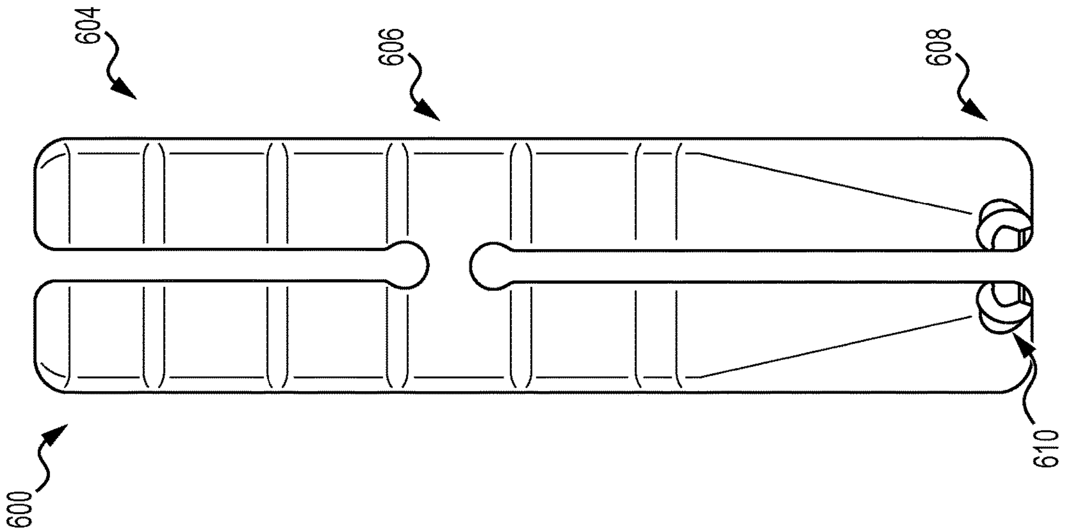

FIGS. 6A and 6B depict a plate inserter 600 in accordance with embodiments of the present disclosure. In some embodiments, the plate inserter 600 includes a body 602 having an upper portion 604, an intermediate portion 606, and a lower portion 608. The upper and lower portions of the body 604, 608 are separated into two independent halves. The intermediate portion 606 joins the two halves of the body 602. The lower portion 608 includes an opening 610 configured to receive the plate 10 therein. In some embodiments, the size of the opening 610 is slightly smaller than the plate 10 such that insertion of the plate 10 into the opening 610 causes outward flexure of the lower portion 608 of the body 602. As a result, the plate 10 is held within the opening 10 by compression caused by the flexure of the body 602. As shown in FIGS. 6A and 6B, the upper portion 604 and at least a portion of the lower portion 608 include a gripping surface 612 configured to be grasped by the hand of a user. In use, the plate 10 is inserted into the opening 610 until it contacts an interior rear surface (not shown) of the body 602. As noted above, the plate 10 is held within the opening 610 by compression of the lower portion 608. A user may then manipulate the plate 10 disposed within the inserter 600 as desired. When it is time for the plate 10 to be removed from the inserter 600, the user squeezes the upper portion 604 inwards, causing the lower portion 608 to flex outward, thus loosening the plate and allowing for its removal.

Figure 7B:
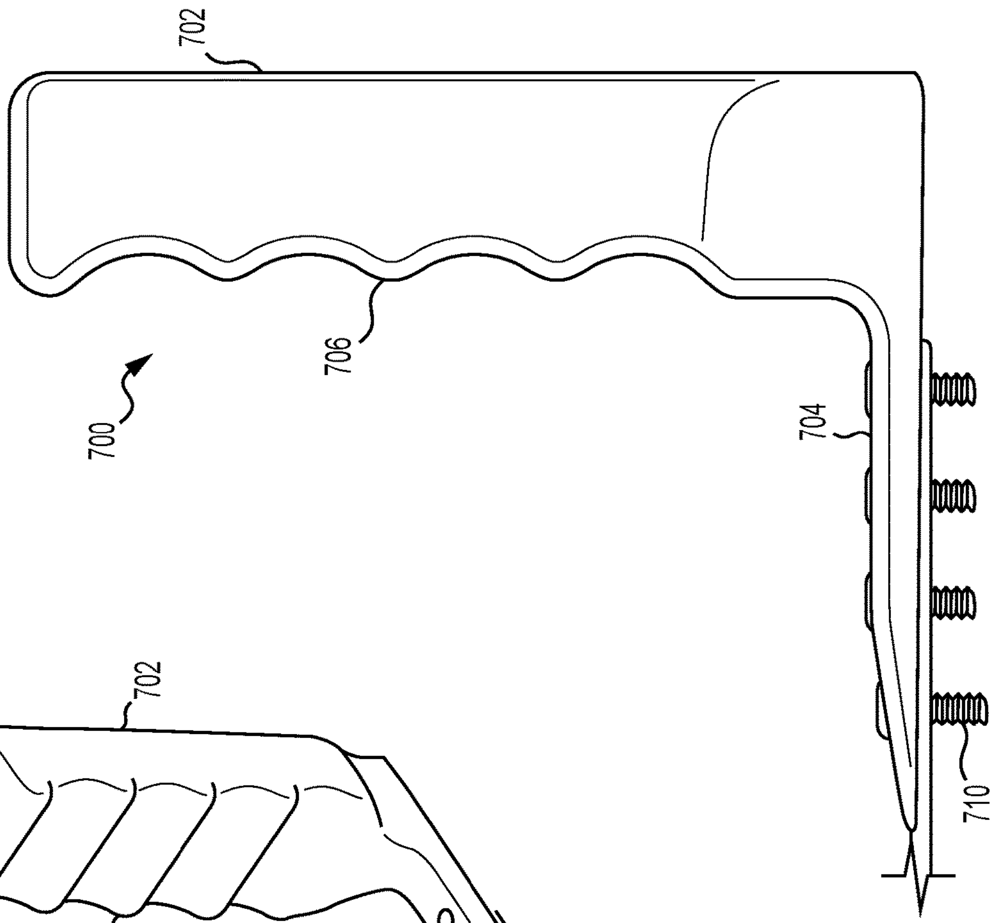
FIGS. 7A and 7B depict an apparatus for inserting a plate in accordance with embodiments of the present disclosure.
Figure 7A:
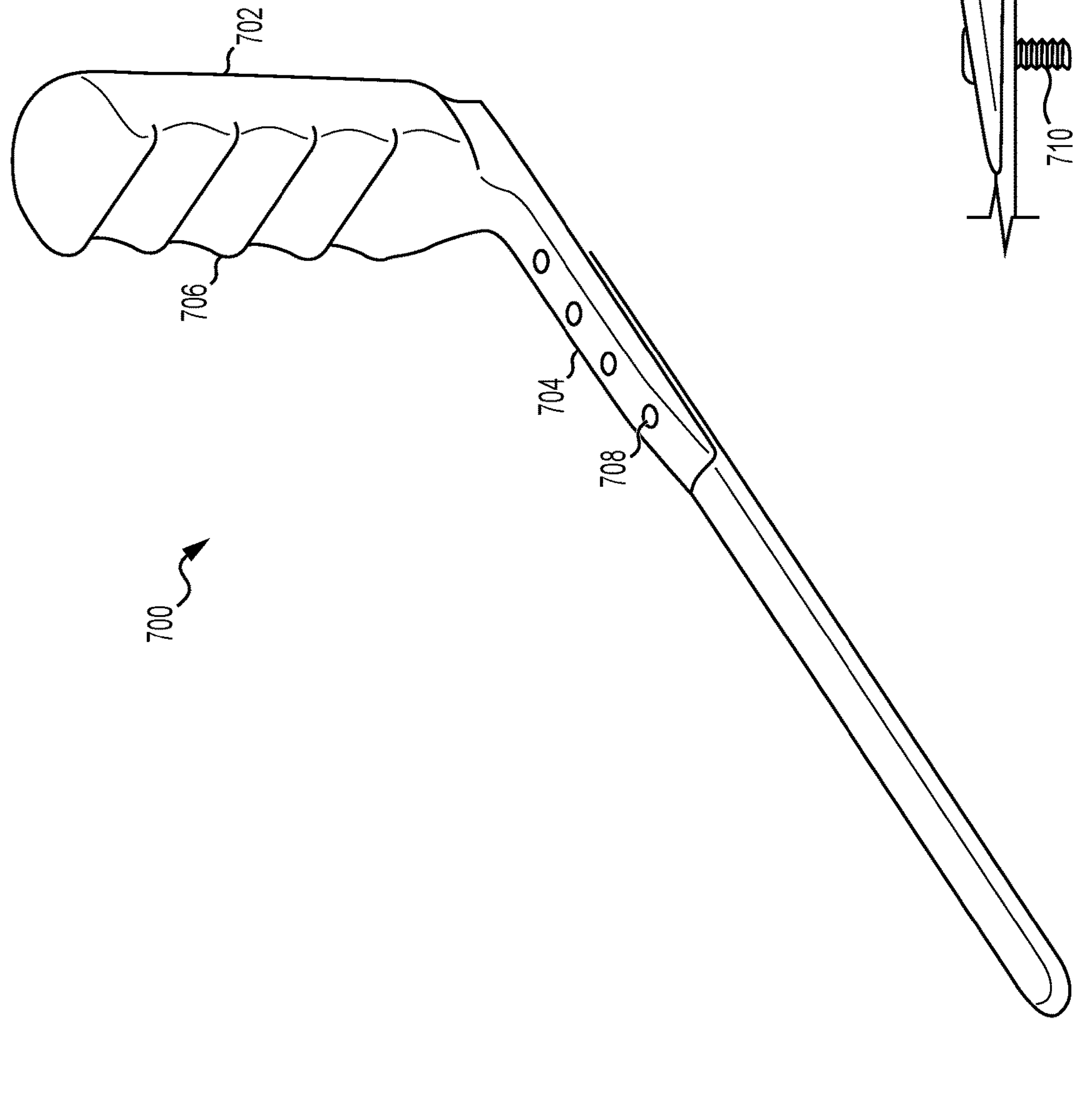

FIGS. 7A and 7B depict a plate inserter 700 in accordance with embodiments of the present disclosure. In some embodiments, the plate inserter 700 includes a body 702 coupled to an engagement portion 704. Together, the body 702 and the engagement portion 704 form an L-shape. In some embodiments, the body 702 and the engagement portion 704 are integrally formed (i.e., monolithic). The body 702 includes a gripping surface 706 configured to be gripped by a user's hand. In some embodiments, the engagement portion 704 includes at least one engagement hole 708 (four shown in FIGS. 7A and 7B) that correspond to at least one of the holes 12 of the plate 10. The engagement holes 708 are configured to receive corresponding fasteners 710 (e.g., screws) such that the fasteners 710 extend through the engagement holes 708 and corresponding holes 12 to couple the plate 10 to the engagement portion 704. The inserter 700 advantageously provides users the ability to use some engagement holes 708 for coupling the plate 10 to the inserter 700 and the remaining engagement holes 708 for securing the plate 10 directly to bone while the plate 10 is still attached to the inserter 700. After the plate 10 has been moved/manipulated as desired, the user removes the fasteners 710 to decouple the plate 10 from the inserter 700.

FIGS. 8A-8E depict a plate inserter 800 in accordance with embodiments of the present disclosure. The plate inserter 800 includes some elements similar to the inserter 400 described above. For example, the inserter 800 includes a body 802 extending from an upper end 804 to a lower end 806, a gripping portion 808, a plate locking mechanism 810 having an actuator 812 that extends through the upper end 804. Also similar to the inserter 400, the actuator 812 includes a rotatable lever 814 coupled to an actuator body 816. The actuator body 816 includes a protruding element 818 that extends radially outward from the actuator body 816 into a groove 820 formed on an interior wall 822 of the body 802. The groove 820 is sloped such that when a user turns the lever 814 (and thus the actuator body 816) in a first direction, movement of the protruding element 818 along the groove 820 forces the actuator body 816 to move downwards. Turning the lever 814 in a second direction opposite the first direction forces the actuator body 816 to move upwards.

However, the inserter 800 differs from the inserter 400 in that the body 802 includes a horizontal portion 813 extending from the lower end 806 of the body. In some embodiment, the horizontal portion 813 includes one or more collets 815 (two shown in FIGS. 8B-8E) configured to be inserted into the holes 12 of the plate 10. Each collet 815 includes a conical portion 817 extending downwards from the horizontal portion 813 and terminating at a collar 819. Each collet 815 also includes two or more slots 821 (one shown in FIGS. 8B-8E due to cross-sectional view) separating the collet 815 into two or more prongs 823. The collets 815 have a maximum diameter that is less than the diameter of the holes 12 so that the collets 815 can be inserted into the holes 12 with relative case.

Figure 8A:
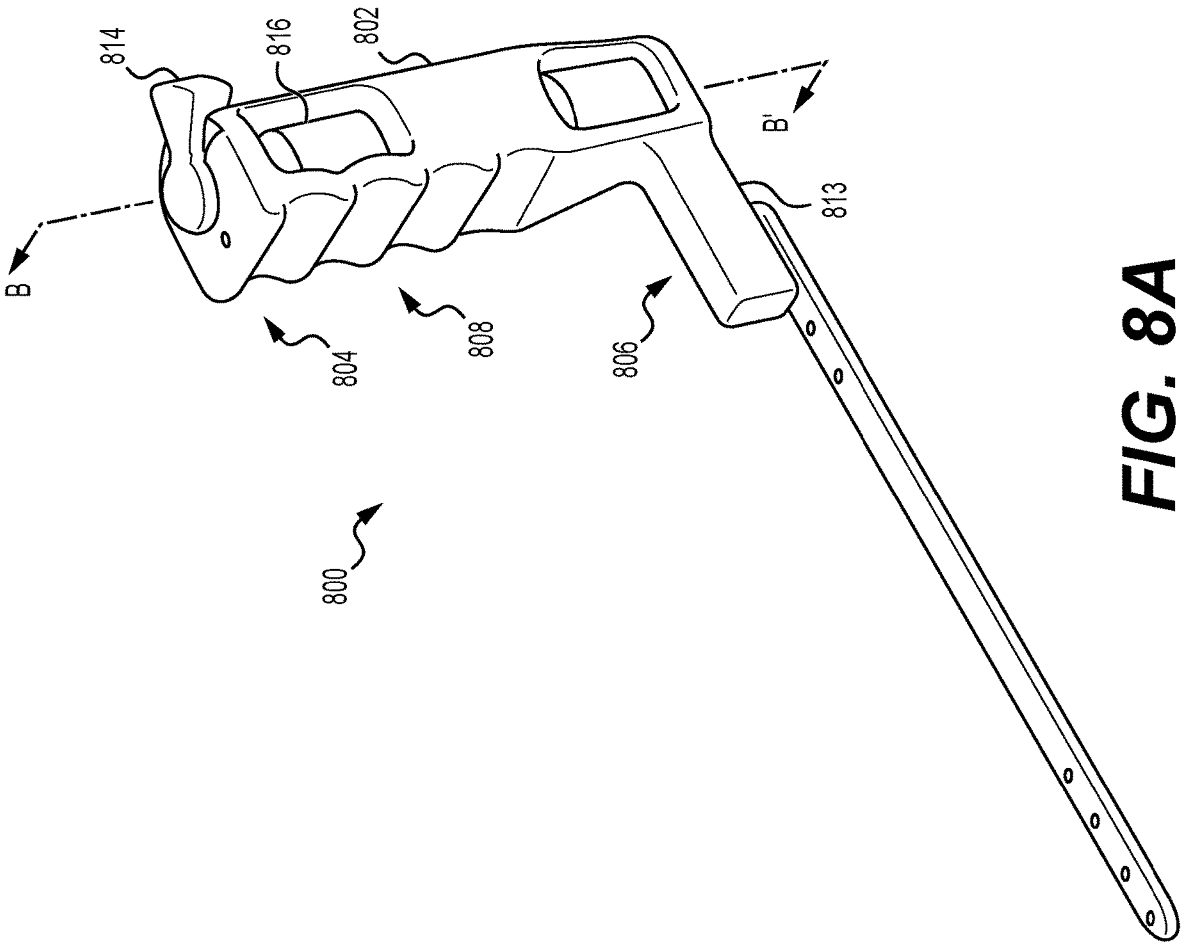
FIGS. 8A-8E depict an apparatus for inserting a plate in accordance with embodiments of the present disclosure.
Figure 8C:
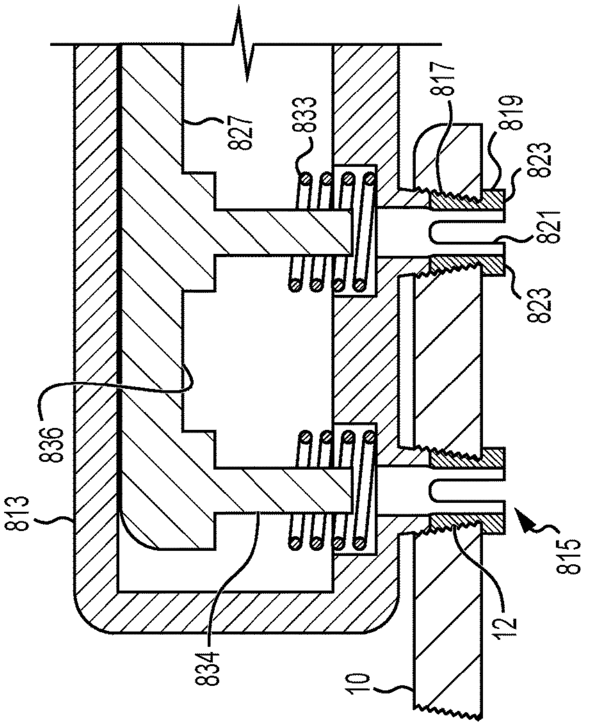
Figure 8B:
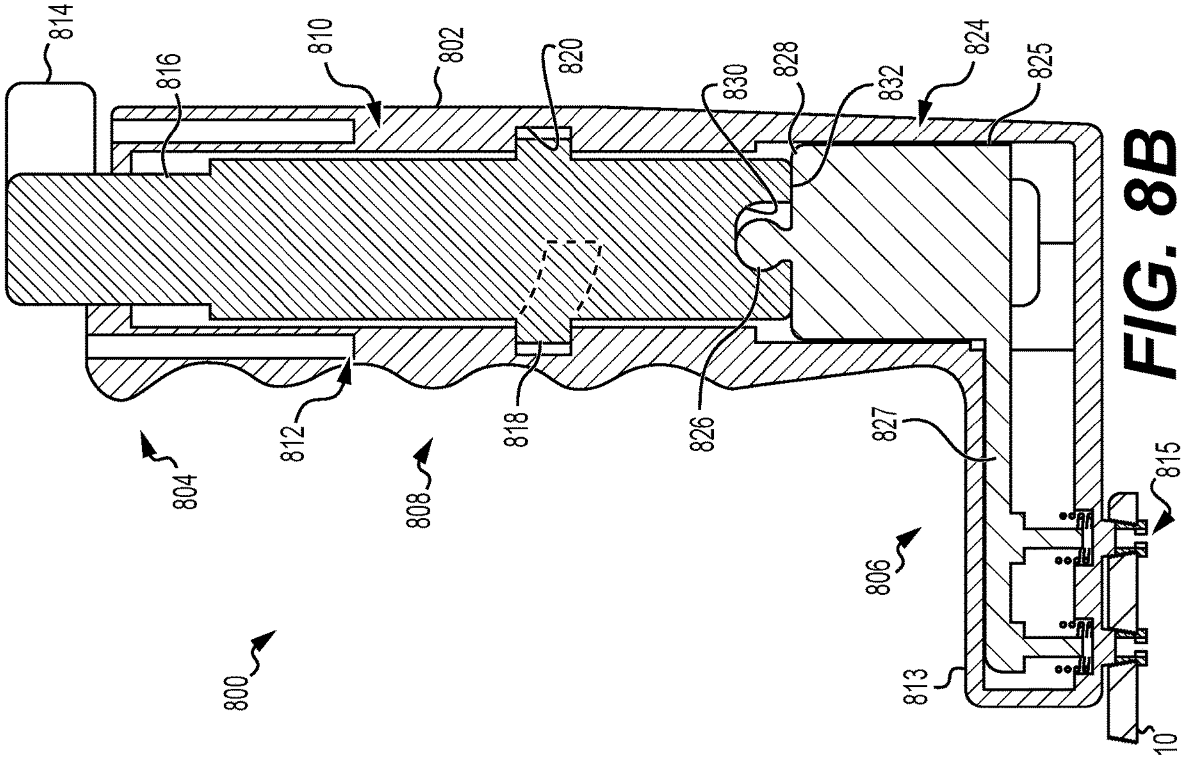
Figure 8E:
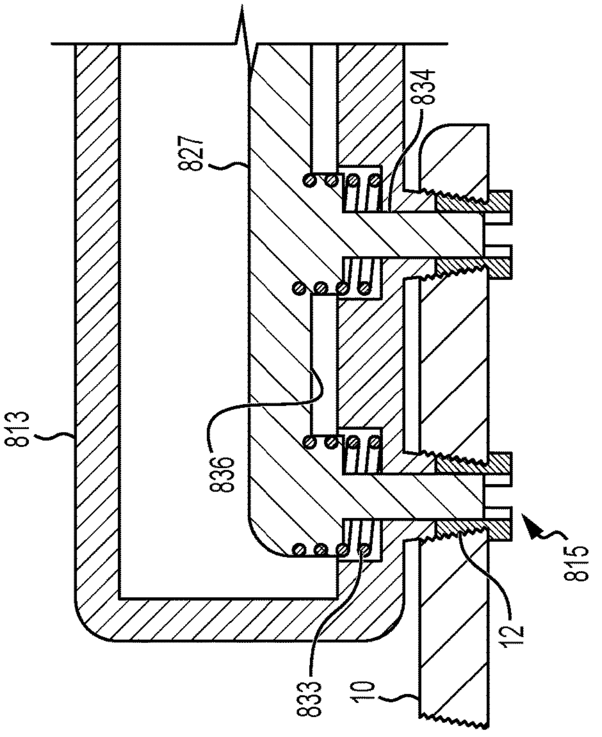
Figure 8D:
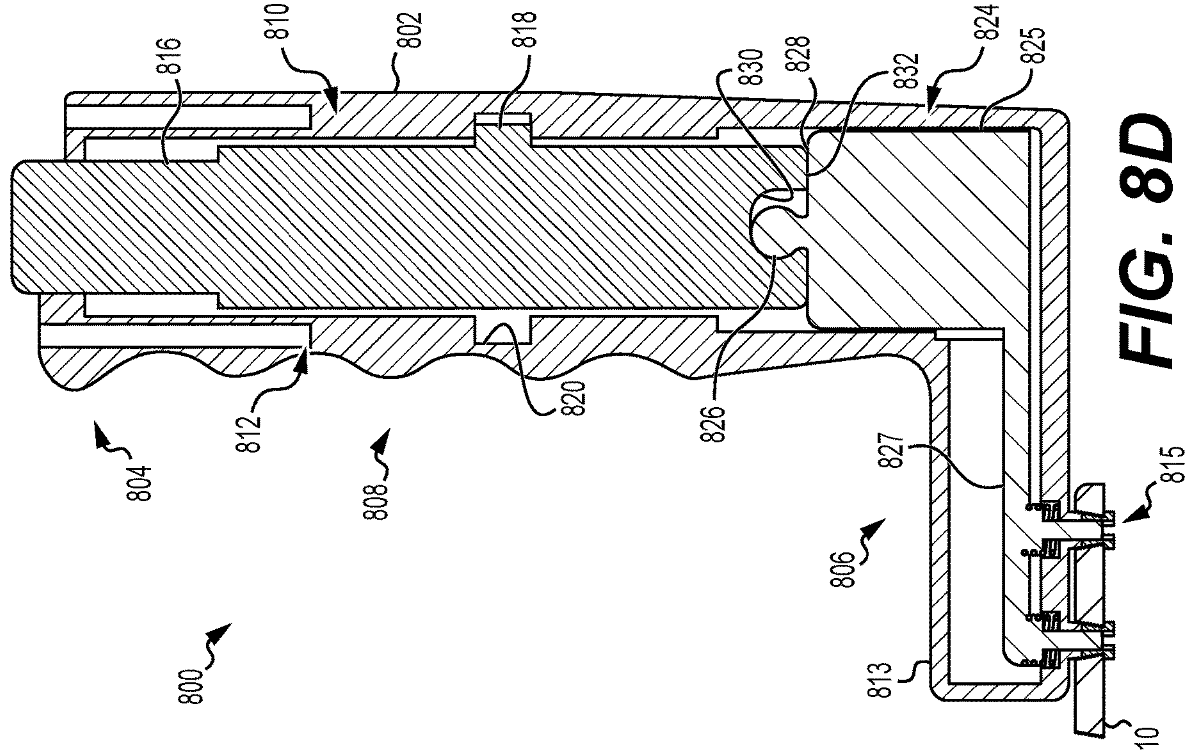

The plate locking mechanism 810 further includes a plate engagement body 824 disposed beneath the actuator body 816. The plate engagement body 824 includes a main body 825 and a horizontal arm 827 extending from the main body 825 into the horizontal portion 813 of the body 802. Similar to the plate engagement body 424, the plate engagement body 824 is coupled to the actuator body 816 in a way that allows the actuator body 816 to rotate relative to the plate engagement body. For example, as shown in FIGS. 8B and 8D, the plate engagement body 824 may include a spherical protrusion 826 extending upwardly from an upper surface 828 of the plate engagement body 824 into a corresponding spherical recess 830 formed in a bottom surface 832 of the actuator body 816. Such a coupling enables the two bodies 816, 824 to be coupled, while allowing for the rotation of the actuator body 816 relative to the plate engagement body 824.

The plate engagement body 824 includes one or more posts 834 (two shown in FIGS. 8B-8E) corresponding to the one of more collets 815. The one or more posts 834 extend downwardly from a bottom surface 836 of the horizontal arm 827 and are configured to engage (i.e., be inserted into) the collets 815. After collets 815 are inserted into the holes 12, the one or more posts 834 are inserted through central openings 829 of the collets 815 to deflect the prongs 823 radially outward. As a result, the plate 10 is locked onto the inserter 800. The collars 819 of the collets 815 provide a retention force so that the plate 10 does not slide off after the expansion of the collets 815.

In use, the inserter 800 is provisionally coupled to the plate 10 by insertion of the collets 815 through the holes 12. Subsequently, the lever 814 is rotated in the first direction to force the actuator body 816 and the plate engagement body 824 downwards so that the posts 834 move into the collets 815, thus forcing the prongs radially outward and locking the plate 10 to the inserter 800. The user may subsequently insert the plate 10 into patient and manipulate the plate 10 as desired. When the user wishes to disengage the plate inserter 800 from the plate 10, the user rotates the lever 814 in the second direction so that the posts 834 retract upwards and out of the collets 815. In some embodiments, one or more springs 833 may be disposed about corresponding ones of the one or more posts 834 to bias the engagement body 824 towards the unlocked position, thus ensuring the posts 834 do not unintentionally drop into the collets 815.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

The invention claimed is:

1. A device for inserting a bone plate to a target site, the device comprising:

a frame extending vertically from an upper end to a lower end, the lower end comprising a plate support base having a groove configured to receive a bone plate;

an actuator handle rotatably coupled to the frame via a pin connection;

an engagement body positioned within the frame and comprising one or more engagement members extending downwardly from a bottom surface of the engagement body and configured to engage one or more holes within the bone plate when the bone plate is positioned within the groove, wherein a lower portion of the actuator handle extends into an opening of the engagement body and comprises a tip extending downwards from a lower surface of the lower portion of the actuator handle; and a retention member pivotably coupled to an upper portion of the actuator handle via a pin connection, wherein the retention member comprises an upwardly extending lip configured to be disposed in a corresponding retention recess formed on an interior of the frame when the device is in an engagement configuration in which the one or more engagement members of the engagement body are engaged with the one or more holes of the bone plate, wherein the engagement configuration is assumed when a user squeezes the actuator handle causing it to pivot about the pin connection and move towards the frame and the lower portion of the actuator handle moves away from a back wall of the opening of the engagement body, causing the tip of the actuator handle to exert a downward force on the engagement body and the one or more engagement members to engage with the one or more holes of the bone plate in the groove.

2. The device of claim 1, comprising a first torsion spring mounted on a post within the frame.

3. The device of claim 2, wherein a free end of the first torsion spring is in contact with the actuator handle, biasing the actuator handle in a disengaged configuration, in which the one or more engagement members of the engagement body are not engaged with the one or more holes of the bone plate.

4. The device of claim 3, wherein, when the one or more engagement members are disengaged from the one or more holes of the bone plate, the actuator handle returns to the disengaged configuration under the biasing force of the first torsion spring.

5. The device of claim 1, comprising a second torsion spring coupled to the actuator handle via a pin connection.

6. The device of claim 5, wherein a free end of the second torsion spring contacts the retention member and is configured to bias the retention member upwards.

7. The device of claim 6, wherein, when the lip of the retention member is disposed within the retention recess under the bias of the second torsion spring, the device is locked in the engagement configuration, allowing the bone plate to be manipulated as desired.

8. The device of claim 1, wherein, when a button disposed in the upper end of the frame is pressed, a lower portion of the button pushes the retention member down, overcoming the biasing force of the second torsion spring thus moving the lip out of the retention recess and disengaging the one or more engagement members from the one or more holes of the bone plate.

9. The device of claim 8, comprising a biasing element disposed between the button and the frame to bias the button upwards such that the button returns to an original state after being pressed down to release the retention member.

10. The device of claim 1, wherein the frame comprises a lip that retains the upwardly extending lip of the retention member when the actuator handle is in the disengaged configuration.

* * * * *